United States Patent [19]

Fuller et al.

[11] Patent Number: 4,946,942

[45] Date of Patent: Aug. 7, 1990

[54] URETHANE-PROTECTED AMINO ACID-N-CARBOXYANHYDRIDES

[75] Inventors: William D. Fuller, San Diego; Michael P. Cohen, Salona Beach, both of Calif.; Fred R. Naider, Staten Island, N.Y.; Murray Goodman, LaJolla, Calif.

[73] Assignee: Bioresearch, Inc., Farmingdale, N.Y.

[21] Appl. No.: 168,087

[22] Filed: Mar. 11, 1988

[51] Int. Cl.$^5$ .................... C07K 1/00; C07D 277/00; C07D 279/00; C07D 281/00; C07D 263/00; C07D 265/00; C07D 267/00

[52] U.S. Cl. .................... 530/335; 530/334; 530/337; 530/333; 548/227; 548/183; 544/97; 544/54; 540/488

[58] Field of Search ............... 530/335, 334, 337, 333; 548/227, 183; 544/97, 54; 540/488

[56] References Cited

U.S. PATENT DOCUMENTS 4,038,282  7/1977  Hirschmann et al. ............. 530/337
4,267,344  5/1981  Halstrom et al. ................... 548/227

OTHER PUBLICATIONS

Akiyama, M., *Tetrahedron Letters*, 28: 2599–2600, 1979.
Shimizu, K., Bull. Chem. Soc. Jpn., 57: 495–499, 1984.
Hirschmann, R., JACS, 93 (11): 2746–2754, 1971.
Halstrom, J., *Peptides* (Eur. Peptide Symp., 12th, 1972), 1973.
Bodanszhy, M., *Principles of Peptide Synthesis*, Springer-Verlag, N.Y.: 25–86, 1984.
Blacklock, T. J., *The Peptides*, 9: 39–102, 1987.
Kricheldorf, Makromol. Chem., 178: 905–939, 1977.

Primary Examiner—Margaret Moskowitz
Assistant Examiner—Susan M. Perkins
Attorney, Agent, or Firm—Larson and Taylor

[57] ABSTRACT

The invention relates to urethane-protected amino acid-N-carboxyanhydride and N-thiocarboxyanhydride compounds which are useful in peptide, polypeptide and protein synthesis. Disclosed herein is the preparation and use of these novel compounds.

72 Claims, 1 Drawing Sheet

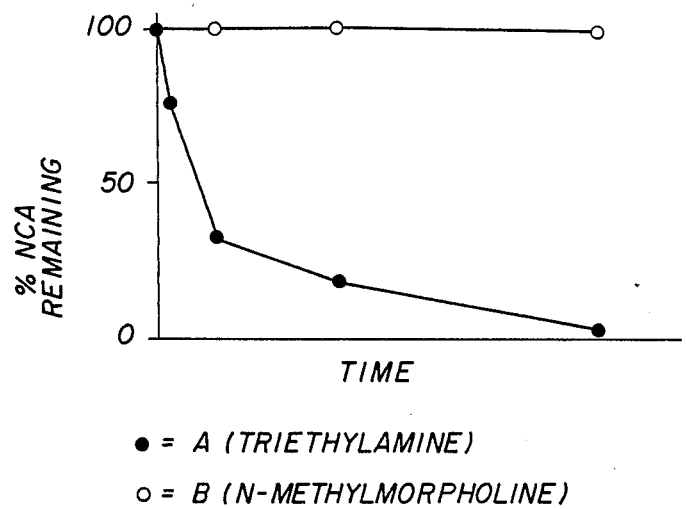

URETHANE-PROTECTED AMINO ACID-N-CARBOXYANHYDRIDES

BACKGROUND OF THE INVENTION (I) Field of the Invention

This invention relates to a novel class of N-protected amino acid-N-carboxyanhydrides and thiocarboxyanhydrides, namely N-urethane protected amino acid-N-carboxyanhydrides and N-urethane protected N-thiocarboxyanhydrides, their preparation and their use in peptide, poly peptide and protein synthesis.

(II) Prior Art

Classically, polypeptides of a defined sequence have been prepared by extremely laborious techniques wherein the intermediates have been isolated after the addition of each amino acid moiety. This has complicated the synthesis and made the preparation of long chain polypeptides and proteins nearly impossible because of low yields, racemization, and/or other side reactions. In 1963, Merrifield (J. Am. Chem. Soc., 85, 2149) and Letsinger and Kornet (J. Am. Chem. Soc., 85, 2045) suggested the use of insoluble polymeric supports for the growing peptide chain. This process, commonly referred to as a solid phase peptide synthesis, permitted the "purification" of the growing peptide chain, without isolating the intermediate.

Heretofore, the widely accepted methods for both classical (liquid phase) and solid phase polypeptide synthesis required the use of a coupling or activating agent to react with the carboxyl group of an otherwise N-protected amino acid to give a carboxyl-activated N-protected amino acid. This activated species would then be used in several ways to promote peptide bond formation. For example, the activated protected amino acid is allowed to react directly with the free amino group of an amino acid, amino acid ester, or amino acid amide to form the peptide bond. This has been the procedure of choice for preparing peptides for many years. The activation step can be accompanied by a number of possible side reactions. For example, where dicyclohexylcarbodiimide (DCC) is the activating reagent, the active molecule may "re-arrange" to an inactive N-acyl urea.

Another disadvantage of the carbodiimide procedure is the formation of insoluble ureas. This is particularly troublesome in solid phase synthesis and is virtually unacceptable in solid phase flow systems. These ureas also cause difficult purification problems in solution phase reactions.

Researchers have alleviated some of the problems associated with in situ activation by first reacting the DCC activated N-protected amino acid with an alcohol or phenol (such as p-nitrophenol, pentachlorophenol, N-hydroxy-succinimide, etc.) to form an "active ester" which may be isolated and purified and then allowed to couple with the free amine of the next amino acid. This approach is not without its shortcomings, however, because the liberated alcohol or phenol may be involved in or promote other side reactions and active ester couplings tend to be sluggish and require long reaction times.

Another common procedure is to form a "symmetrical anhydride" by allowing two equivalents of N-protected amino acid to react with one equivalent of DCC, filtering the DCU formed and then allowing the "symmetrical anhydride" to couple with the free amine group of the next amino acid. This procedure has the urea problem in addition to requiring use of twice as much of an expensive N-protected amino acid.

Some researchers have recently begun to use carbodiimides that form soluble ureas after coupling, but these are still prone to re-arrangement to N-acyl ureas.

Various types of N-protecting groups have been proposed for use in peptide synthesis, but the most widely accepted class of N-protecting groups are the urethanes. Urethanes are broadly acknowledged to provide a high degree of protection, minimize racemization, are readily prepared, and are stable to storage. Urethane-protecting groups can be prepared which are labile to mild acid (i.e. t-butyloxycarbonyl), strong acid (i.e., benzyloxycarbonyl), extremely mild acid 2(p-biphenylyl)isopropyloxycarbonyl, anhydrous base (i.e., 9-fluorenylmethyloxycarbonyl), and so forth.

Urethane-protected amino acids are commonly prepared by reaction of an alkyl, aryl or aralkylchloroformate (or other suitably activated formate or carbonate) with the amino acid in the presence of alkali metal hydroxide or carbonate in a mixed aqueous/organic solvent system (i.e., Schotten-Baumann conditions). After acidification of the reaction mixture, the urethane-protected amino acid is extracted into an organic solvent leaving all side products in the aqueous phase. After crystallization, these compounds are used for peptide bond formation as described above.

A particularly interesting type of reactive derivative of amino acids for use in peptide bond formation are the so-called N-carboxyanhydrides or N-thiocarboxyanhydrides, such as:

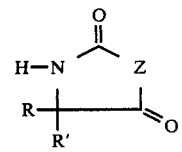

wherein R, R' are typically hydrogen or the side chains (or protected side chains) of the common amino acids, and Z is oxygen or sulfur.

Amino acid-N-carboxyanhydrides (it is understood that the term N-carboxyanhydride in this specification and appended claims is to include the N-thiocarboxyanhydrides) are well-known and react readily with most free amines. A primary advantage of N-carboxyanhydrides (NCA's) and even protected NCA's for use in peptide bond formation is the fact that they are potent acylating agents (see Peptides, Vol. 9, page 83). They also generally give higher yields of peptides than DCC or N-hydroxysuccinimide (OSu) ester coupling procedures. But NCA's have not found widespread use in polypeptide synthesis because of the lack of ability to control or limit the coupling reaction. Once an NCA reacts with the free amine of an amino acid, carbon dioxide is immediately liberated and a dipeptide is formed which also contains a free amine. This amine will subsequently react with another NCA to form a tripeptide, and so on. This reaction has allowed amino acid N-carboxyanhydrides to find extensive use in the formation of poly α-amino acids but has virtually precluded their use in sequential polypeptide formation. Hirschmann, et al (The Controlled Synthesis of Peptides in Aqueous Medium. VIII.) The Preparation and Use of Novel α-Amino Acid N-Carboxyanhydrides. J.A.C.S., 93:11, 1971, pg. 2746-2774) have succeeded in using amino acid N-carboxyanhydrides for the preparation of di- and tripeptides in aqueous-organic solvent systems by careful control of temperature, pH, salt, and organic solvent of the reaction mixture. However, this procedure is limited to small peptides because of the chemistry of NCA's described above. Furthermore, the products obtained from these solution phase reactions must be extensively purified prior to being used for the preparation of larger peptides.

A variety of N-substituted amino acid N-carboxyanhydrides have been reported in the literature such as N-methyl, N-benzyl, N-acetyl, N-nitrophenylsulfenyl, N-xanthyl, 4,4'-dimethylbenzhydryl, trityl, and the like. Several of these substituted-NCA's have been proposed for use in sequential peptide synthesis and particularly for solid phase peptide synthesis, but none have gained acceptance for general use by peptide chemists.

Kricheldorf (Angew. Chem. Acta 85, 86–87, (1978)) proposed the use of o-nitrophenylsulfenyl (NPS) substituted NCA's for use in sequential polypeptide synthesis. These were prepared by the reaction of o-nitrophenylsulfenylchloride with a N-carboxyanhydride in the presence of triethylamine. Subsequently, it has been shown that triethylamine promotes the racemization of NPS- NCA's. In addition, oligomerization due to the action of triethylamine on the NCA, requires that very stringent reaction conditions must be employed (i.e. temperature <0° C. and very slow addition of triethylamine to the reaction mixture) during NPS-NCA synthesis. Halstrom, et al, (Z. Physiol. Chem. 355, 82–84, (1974)) consequently proposed the synthesis of NPS-NCA's by reaction of phosgene with the NPS-amino acid but the yields were very low (about 20%). Once prepared, NPS-NCA's are difficult to store, and tend to "bleed off" the protecting group during condensation, giving rise to multiple coupling, and other side reactions. Also, the nitrogen of the resulting NPS protected peptide possesses substantial nucleophilicity and may undergo additional condensation reactions.

Block and Cox ("Peptides, Proc. of the 5th Europ. Symp., Oxford, Sept. 1962". Pergamon Press 1963, Ed. G. T. Young, pp. 84–87.) proposed the use of N-trityl amino acid-N-carboxyanhydrides for use in peptide synthesis, although they were only able to prepare the simplest N-tritylamino acid NCA's (i.e. glycine and alanine). These compounds were prepared by the reaction of a N-trityl-amino acid with phosgene. By this procedure, they were also able to prepare N-acetyl-glycine-NCA. These researchers recognized the potential usefulness of t-butyloxycarbonyl glycine N-carboxyanhydride and benzyloxycarbonyl glycine N-carboxyanhydride but were unsuccessful in their attempts to prepare them and concluded that urethane-protected amino acid N-carboxyanhydrides could not be made ! Even if all the N-trityl-NCA's could be prepared it is well known that the use or trityl protection of amino acids in various condensation methods produces low yields because of the considerable steric hindrance imposed by the trityl group. The trityl group is also extremely sensitive to acid which makes the preparation of the trityl-NCA difficult and tends to "bleed off" during normal solid phase manipulations.

Halstroem & Kovacs (*Acta Chemica Scandinavica, Ser. B* 1986, BYO(6), 462–465 and U.S. Pat. No. 4,267,344) also recognized the advantages and the potential usefulness of N-protected amino acid N-carboxyanhydrides and were able to prepare several N-substituted NCA's which they felt would fulfill all the requirements necessary for use in peptide synthesis. They were able to prepare a number of 9-xanthyl (and related) substituted amino acid N-carboxyanhydrides. These compounds were claimed to be preparable by the direct condensation of xanthydrol with the appropriate NCA in refluxing benzene, toluene, xylene or other alkyl benzene. The water formed during condensation was removed azeotropically. This procedure suffers from the instability of NCA's to heat and to water, consequently leading to low yields and potentially impure products. These compounds may also be prepared by the reaction of phosgene (or phosgene equivalent) with the corresponding 9-xanthyl-amino acid and, in fact, most of the substituted NCA's in this class have been prepared by this procedure.

When used in peptide synthesis the 9-xanthyl-NCA's have been found to react sluggishly requiring as long as 5 hours at 50° C. in solution and 24 hours at 25° C. in solid phase synthesis. This is likely due to the steric hindrance of the 9-xanthyl group and/or the deactivating effect. Another problem associated with 9-xanthyl protection of amine groups is that the nitrogen atom of the 9-xanthyl amino acid formed after the coupling reaction is still nucleophilic and capable of undergoing subsequent condensation reactions. These groups will also tend to bleed off during manipulation. Consequently, to date, substituted amino acid N-carboxyanhydrides of this or any other type have not found widespread use in peptide synthesis, particularly in solid phase peptide synthesis.

Kricheldorf, (*Makromol. Chem.* Vol. 178, pp 905–939, 1977) has described a method for the preparation of methoxycarbonyl glycine NCA and ethoxycarbonyl glycine NCA. However, Kricheldorf also reports that this procedure was incapable of producing urethane-protected NCA's of amino acids having a side chain other than hydrogen because of steric hindrance.

It is an object of the invention, therefore, to provide the heretofore unobtainable urethane-protected N-carboxyanhydrides and N-thiocarboxyanhydrides of the higher amino acids.

Another object of the invention is to provide procedures for the preparation of pure, crystalline, stable urethane-protected amino acid N-carboxyanhydrides and urethane-protected N-thiocarboxyanhydrides.

Yet another object of the invention is to provide a method for the synthesis of polypeptides utilizing pure, crystalline urethane-protected amino acid-N-carboxyanhydrides, which synthesis offers the following major advantages over conventional methods of polypeptide synthesis:

(1) Pre-activation of the carboxyl group to be coupled is unnecessary, thus eliminating side products generated by conventional activating molecules.

(2) No additives such as N-hydroxybenzotriazole are needed to inhibit racemization.

(3) The only co-product from the coupling reaction is carbon dioxide.

(4) These N-protected carboxyl activated amino acids are stable, storable, crystalline materials and, therefore, facilitate and simplify both solid and liquid phase peptide synthesis, especially in automated peptide synthesizers, by eliminating the need for activations, filtrations, and couplings prior to the peptide bond forming reaction. The purification of peptides prepared in solution is greatly facilitated by the use of these novel compounds because of the lack of by-products produced by coupling agents.

(5) The procedure will provide, after coupling, the widely accepted urethane-protecting groups on the amino function of the growing peptide chain which may then be manipulated by conventional techniques.

SUMMARY OF THE INVENTION

These objects are obtained by a urethane-protected amino acid-N-carboxyanhydride or N-thiocarboxyanhydride having the structure:

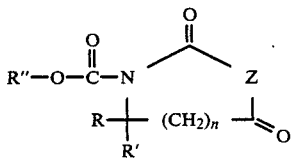

wherein R and R' are hydrogen, alkyl, cycloalkyl, substituted alkyl, substituted cycloalkyl, aryl, or substituted aryl and at least one of R and R' is other than hydrogen; R'' is alkyl, aryl, substituted alkyl or substituted aryl; Z is oxygen or sulfur; and n is 0, 1, or 2.

The preferred R, R' and R'' groups are alkyl groups, including cycloalkyl groups, of 1 to 12 carbon atoms or more, aryl groups of 6 to 20 carbon atoms or more including aralkyl and alkaryl groups of 7 to 20 carbon atoms or more. Exemplary of suitable alkyl groups are methyl, ethyl, propyl, isopropyl, isobutyl, butyl, t-butyl, hexyl, cyclopentyl, cyclohexyl, heptyl, octyl, and the like. Illustrative of suitable aryl groups are phenyl, methylphenyl, ethylphenyl, naphthyl, methylnaphthyl, anthracyl and the like. Examples of suitable aralkyl groups include benzyl, p-methoxybenzyl, 9-fluorenylmethyl, phenylethyl, and the like. Suitable alkaryl groups include tolyl, ethylphenyl, isopropylphenyl and the like. The R, R' and R'' groups may also be substituted with noninterfering groups such as fluoro, methoxy, t-butoxy, carboxyl, amido, benzyloxy, hydroxy, substituted amino, substituted hydroxy, sulfur, substituted sulfur, chloro, bromo, and the like. R and R' are typically the protected or unprotected groups attached to the α-carbon atom (side chains) of amino acids or analogues thereof.

In most instances, one of R or R' is usually H while the other is the side chain on the α-carbon atom of an amino acid such as lysine, leucine, arginine, serine, aspartic acid, alanine, asparagine, cysteine, cystine, glutamic acid, histidine, glutamine, isoleucine, methionine, norleucine, ornithine, phenylalanine, threonine, tryptophan, tyrosine, valine, β-alanine, homoserine and the like. Exemplary of such side chains are:

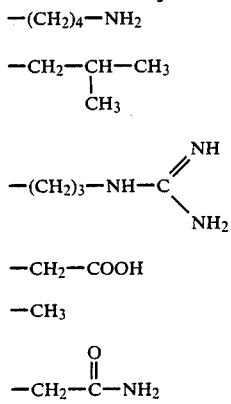

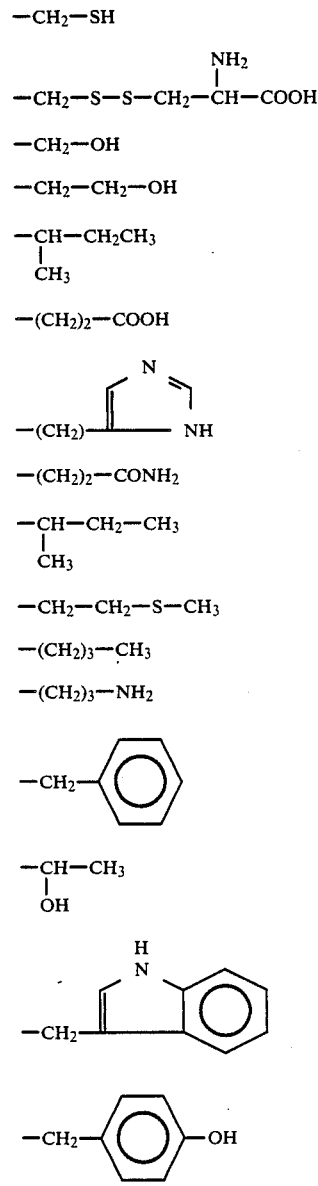

These side chains may be protected as required, using common techniques and protecting groups well known to one skilled in the art, such as the commonly employed amino, hydroxy, thiol and carboxy protecting groups.

The compounds of the invention also include instances where both R and R' are side chains attached to the α-carbon of an amino acid as, for example, in the case of isovaline where one of R or R' is —CH$_2$CH$_3$ and the other is methyl.

The compounds of the invention also include instances where R and R' are part of a cyclic structure as, for example, in the case of 1-amino-1-cyclohexane carboxylic acid.

The compounds of the invention also include examples such as ortho-amino benzoic acid or 1-amino-2-carboxy cyclohexane wherein carbon atoms from the R or R' groups are part of a cyclic ring.

Another aspect of the invention involves an improvement in the synthesis of a polypeptide chain wherein a N-protected amino acid component is deprotected and the deprotected amino acid component is allowed to react with a second similar or dissimilar activated N-protected amino acid component and the process repeated until the desired polypeptide is obtained, said improvement comprising using as the activated N-protected amino acid component in at least one of said reactions a compound having the structure:

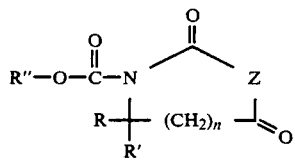

wherein R, R', R", Z and n are as designated above.

Yet another aspect of the invention involves an improvement in the solid phase synthesis of a polypeptide chain on an insoluble solid support wherein a N-protected amino acid component is coupled by condensation reaction to an insoluble solid support containing substituent groups reactive with the carboxyl terminus end of said amino acid component, the coupled N-protected amino acid component is deprotected, a second similar or dissimilar activated N-protected amino acid component is coupled to said deprotected amino acid compound, and the process repeated until the desired polypeptide is obtained, said improvement comprising using as the activated N-protected amino acid component in at least one of said reactions a compound having the structure:

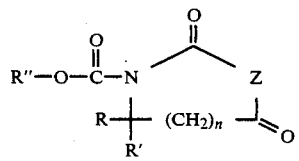

wherein R, R', Z and n are designated above.

Included as a further embodiment of the invention is the method of preparing the urethane-protected amino acid-N-carboxyanhydrides of the invention which comprises the reaction of an amino acid N-carboxyanhydride having the structure:

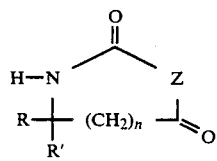

wherein R, R', Z and n are as designated above, with a haloformate (or other suitably reactive formate, such as azido formate) having the structure:

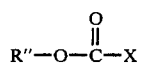

wherein X is chlorine, bromine, fluorine, azide, or the like, and R" is alkyl, aryl, or aralkyl, in an inert diluent, under anhydrous conditions and in the presence of N-methylmorpholine. It has been surprisingly found that utilizing an inert diluent, anhydrous conditions and selecting N-methylmorpholine as the base in this reaction avoids polymerization of N-carboxyanhydrides and otherwise enables the production of the heretofore unobtainable urethane-protected NCA's and NTA's of higher amino acids.

DETAILED DESCRIPTION OF THE INVENTION

The amino acid N-carboxyanhydrides (NCA's) and N-thiocarboxyanhydrides (NTA's) which serve as starting materials for the preparation of the N-urethane protected NCA's and NTA's of the invention may be prepared by a number of procedures well known to one skilled in the art. See for example: Fuller et. al. Biopolymers 15, No. 9, 1869-1871 (1976); Kricheldorf, Chem. Ber. 104, 87-91 (1971); and Halstrom and Kovacs, Acta Chemica Scandinavica, B40, 462-465 (1986).

While urethanes in general may be used as protecting groups for nucleophilic atoms, only a few have found widespread use in peptide synthesis, for example, t-butyloxycarbonyl (Boc); benzyloxycarbonyl (Cbz); and 9-fluorenomethyloxycarbonyl (FMOC). Consequently, amino acid N-carboxyanhydrides or N-thiocarboxyanhydrides substituted with these protecting groups are of particular interest. Accordingly, very useful molecules for peptide synthesis are the NCA's of L-α-amino acids protected by one of the abovementioned protecting groups, such as:

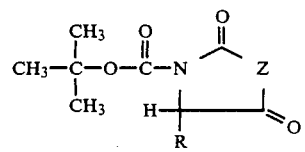

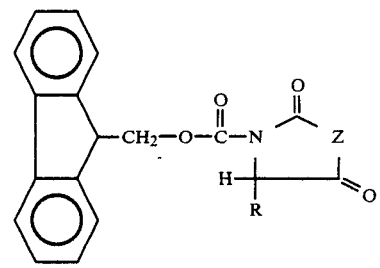

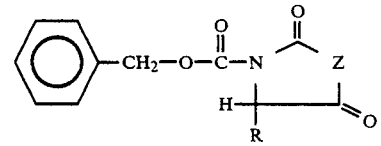

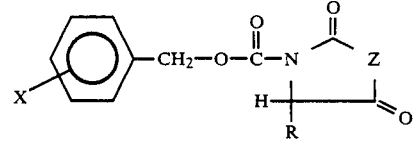

wherein R is the side chain of an α-amino acid, Z is O or S, and X is methoxy, chloro or the like.

As aforementioned, the N-urethane protected NCA's of the invention are unobtainable by the reaction of phosgene with the N-urethane protected amino acid as described by Block and Cox ("Peptides, Proc. of the 5th Europ. Symp., Oxford, Sept. 1962". Pergamon Press 1963, Ed. G. T. Young, pp. 84-87.); nor are N-urethane protected NCA's of the higher amino acids obtainable by the synthesis described by Kricheldorf (*Makromol. Chem.*, Vol. 176, pp 905–939, 1977). It has been found that urethane-protected NCA's and NTA's may be prepared by the reaction of a previously synthesized NCA or NTA with the appropriate haloformate in an anhydrous, non-interfering solvent with the use of N-methylmorpholine as base. The reaction is preferably carried out below room temperature. Useful solvents for the reaction are tetrahydrofuran, ethyl acetate, methylene chloride, toluene, benzene, dioxane, and the like.

Thus, the novel urethane-protected amino acid N-carboxyanhydrides and N-thiocarboxyanhydrides of the invention may be prepared by dissolving an NCA in a non-interfering solvent (such as toluene) and cooling the resulting solution with stirring. The desired haloformate (e.g. benzylchloroformate) is then added all at once. To this mixture is added N-methylmorpholine which scavenges the hydrochloric acid formed during condensation thus promoting the condensation reaction. Under these conditions, polymerization is not initiated. Since there is no fear of polymerization, the base can be used in excess and the resulting urethane protected NCA's are easily isolated by crystallization.

As a result of these discoveries, virtually any urethane protected NCA (or NTA) can be prepared easily in high yield with only minimal precaution for exclusion of moisture. The process is readily scaled up and provides products which are highly crystalline, are readily purifiable by simple techniques (i.e. crystallization), and are stable to storage (completely stable at 25° C. for at least 6 months and probably much longer). Thus, these materials can be weighed, shipped, and stored for use in peptide synthesis without fear of decomposition.

The major advantage that the urethane-protected NCA's offer over other N-substituted NCA's is that after they are used to form a peptide bond, the resulting peptide is protected on the N-terminus by one of the widely accepted urethane protecting groups commonly used in peptide synthesis. These protecting groups are well known by those skilled in the art to provide the best available protection to the amine group of a growing peptide chain.

Thus, the use of urethane-protected N-carboxyanhydrides will offer all the advantages of the unsubstituted NCA's (high reactivity, freedom from formation of undesired rearrangement products, and $CO_2$ as the only by product) but with none of the disadvantages of the unsubstituted NCA's (i.e. instability polymerization, and multiple condensations) which have limited their use to carefully controlled aqueous conditions. Consequently, the invention provides a storable, yet highly reactive, preactivated reagent, which yields minimal side products during peptide bond formation. The invention also provides the widely accepted, well understood, urethane protection on the nitrogen of the N-terminus of the peptide after the condensation reaction.

While the urethane-protected amino acid-N-carboxyanhydrides of the invention can be used in the synthesis of polypeptides by classical methods using a series of deprotection and coupling reactions, they undoubtedly will find more extensive use in solid phase polypeptide synthesis. It should be understood that the term "polypeptides" as used in the specification and appended claims is meant to include peptides and proteins. Also, it should be understood that the present invention contemplates sequential peptide synthesis wherein N-protected amino acids other than the urethane-protected amino acid-N-carboxyanhydrides are employed as well as at least one urethane-protected NCA of the invention. In practice, however, the N-protected amino acid component used in each sequence will more than likely be the urethane-protected NCA's of the invention.

In solid phase polypeptide synthesis, an insoluble solid support or matrix, advantageously in bead form, is used. Such solid supports can be any of the solid-phase polymeric substrates conventionally employed for the synthesis of polypeptides. Typical of such polymeric resins are crosslinked polystyrene resins, glass beads, clays, celite, crosslinked dextran, polyacrylamides, polyamide resins and similar insoluble solid supports which either naturally contain reactive sites for coupling with the amino acid components or which can be provided with such reactive sites.

If desired, the solid phase polypeptide synthesis of the invention can be carried out in a flow reactor under pressure as described in U.S. Pat. No. 4,192,798, hereby incorporated by reference, but the use of superatmospheric pressures is not essential.

Several preliminary operations are necessary before the solid phase synthesis of a peptide can be started. First, the supporting resin containing the C-terminal amino acid component of the proposed peptide chain must be prepared. This can be accomplished by any of a number of procedures known to one skilled in the art. Many of these N-protected amino acids, linked to various solid supports, are articles of commerce and may be purchased as desired.

The remaining synthesis to form the desired polypeptide sequence is carried out as follows. Before coupling of the second amino acid residue can take place, the first residue already on the support must be deprotected. Deprotection of the first amino acid residue on the resin as well as of each of the subsequently coupled amino acid residues can be carried out by contacting the protected amino acid residue with an appropriate deprotecting agent. The deprotecting agents employed for this purpose are well known to those of ordinary skill in the art of peptide synthesis and the particular deprotecting agent employed in any given instance will depend, of course, upon the protecting group on the amino acid/resin. For example, if the protecting group is t-butyloxycarbonyl, trifluoroacetic acid in dichloromethane or hydrochloric acid in a suitable solvent such as dioxane may be used. On the other hand, if the protecting group is 9-fluorenylmethyloxycarbonyl, basic conditions such as piperidine in DMF will be the preferred method. The concentrations of the particular deprotecting agent in the solvent will vary depending again upon the particular protecting agent employed but will ordinarily range from about 5 to 50% by volume.

After the deprotecting step, the resin is washed with a suitable solvent in order to remove excess deprotecting agents. If the deprotecting agent is an acid the peptide on the resin must be neutralized by washing with an appropriate base such as triethylamine in a solvent such as dichloromethane. Any excess triethylamine and triethylammonium chloride or trifluoroacetate formed may be removed by repeated washings with a suitable solvent such as dichloromethane or dimethylformamide. The free amine, thus prepared, is now ready for coupling with the next N-protected amino acid.

If the next N-protected amino acid is a urethane-protected amino acid N-carboxyanhydride of the invention, it need not be activated and can be reacted directly with the support now containing an unprotected resin bound amino acid. If, however, the N-protected amino acid component is to be coupled by more conventional procedures, it will be necessary to first activate, that is, convert it into a reactive form, for instance, by converting the amino acid into an anhydride or by activation with dicyclohexylcarbodiimide, carbonyldiimidazole or other activating agents. In general, an excess of the activated N-protected amino acid component is employed in the reaction.

After the coupling of the second protected amino acid component to the first amino acid component, the attached protected dipeptide is then deprotected, neutralized if necessary, and washed as described above before coupling of the next amino acid derivative is effected. This procedure is repeated until the desired sequence of amino acids has been assembled on the insoluble support.

Because of the lack of undesirable side reactions and byproducts ($CO_2$ being the only one) in the urethane protected NCA coupling, and because of their stability, the excess urethane protected NCA used in the coupling reactions may be easily recovered, recrystallized and re-used, thus markedly increasing the cost effectiveness of these materials.

The completed peptide can be removed from the insoluble support by any of the standard methods as, for instance, by cleavage with anhydrous hydrogen fluoride, transesterification, aminolysis, etc.

After cleavage, the resulting peptide is found to be remarkably homogeneous and to require no or minimal purification. Because of the very low contamination of byproducts overall yields are found to be surprisingly high and whatever purification is necessary can be carried out with relative ease. Such purifications are preferably carried out by partition chromatography, ion exchange chromatography or a combination of both. Such procedures are well-known to one skilled in the art of peptide synthesis.

EXAMPLE I

N-Carboxyanhydride Decomposition as a Function of Base

A. Valine N-carboxyanhydride (72 mg) was dissolved in dry, distilled tetrahydrofuran (2 mL) and triethylamine (30 μl) added. The disappearance of the NCA was followed by infrared spectroscopy.

B. Valine N-carboxyanhydride (72 mg) was dissolved in tetrahydrofuran (2 mL) and N-methylmorpholine (25 μl) added. The disappearance of the NCA was followed by infrared spectroscopy.

The results of A and B are shown in the graph of FIG. 1:

EXAMPLE II

N-(9-Fluorenylmethyloxycarbonyl)-L-Alanine-N-Carboxyanhydride

A. A mixture of L-alanine (40.3 g, 0.45 mol) and phosgene (275 mL of 3.3M solution in tetrahydrofuran, 0.90 mol) was stirred at 62°–64° C. for 4 hours. The resulting solution was allowed to cool to room temperature, filtered, and the volatiles removed under reduced pressure. The resulting oil was dissolved in 100 mL of tetrahydrofuran and 300 mL of hexane was added with stirring, followed by cooling to −20° C. The yield of L-alanine N-carboxyanhydride was 35.79 g (69%).

B. A solution of N-methylmorpholine (8.15 g, 80.5 mmol) in toluene (50 mL) was added to a 0° C. mixture of L-alanine-N-carboxyanhydride (8.84 g, 76.8 mmol) and 9-fluorenylmethyloxycarbonyl chloride (19.9 g, 76.8 mmol) in toluene (200 mL). The reaction mixture was stirred at 0° C. for 2 hours and filtered. The volume of solvent was reduced to 20 mL and crystallization occurred upon addition of 100 mL of hexane to give 21.4 g (82%) of crude 9-fluorenylmethyloxycarbonyl-L-alanine-N-carboxyanhydride. The product was purified by trituration with cold diisopropyl ether followed by recrystallization from ethyl acetate/hexane: mp 106°–107° C.; IR ($CH_2Cl_2$) 1870, 1801, 1740 cm$^{-1}$; NMR ($CDCl_3$) δ 6.90–7.80 (m, 8H), 3.95–4.55 (m, 4H), 1.35 (d, J=7 Hz, 3H). Anal. Calcd for $C_{19}H_{15}NO_5$: C, 67.65; H, 4.48; N, 4.15. Found: C, 67.73; H, 4.65; N, 4.19.

EXAMPLE III

N-(9-Fluorenylmethyloxycarbonyl)-L-Leucine-N-Carboxyanhydride

A. L-Leucine-N-carboxyanhydride was prepared from L-leucine in 78% yield by the procedure outlined in Example IIA.

B. A mixture of L-leucine-N-carboxyanhydride (9.2 g, 58.4 mmol) and 9-fluoroxylmethyloxycarbonyl chloride (15.1 g, 58.4 mmol) in toluene (125 mL) was cooled to 0° C. and a solution of N-methylmorpholine (6.5 g, 64 mmol) in 20 mL of toluene was added dropwise. The reaction mixture was stirred at 0° C. for 2.5 h, filtered, and the volume of solvent reduced to 20 mL. Hexane (480 mL) was added, and the solution was cooled to −20° C. overnight, to give 18.8 g (85%) of N-(9-fluorenylmethyloxycarbonyl)-L-leucine-N-carboxyanhydride. An analytical sample was obtained by recrystallization from ether/methylene chloride/hexane: mp 118°–120° C.; NMR ($CCl_4$) δ 7.35–7.91 (m, 8H); 4.72 (t, J=7 Hz, 2H); 4.58 (m, 3H); 4.37 (t, J=7 Hz, 1H); 2.05 (m, 2H); 1.09 (t, J=6 Hz, 6H). Anal. Calcd for $C_{22}H_{21}NO_5$: C, 69.64; H, 5.58; N, 3.69. Found: C, 69.08; H, 5.97; N, 3.70.

EXAMPLE IV

N-α-(9-Fluorenylmethyloxycarbonyl)-N-ε-t-Butyloxycarbonyl-L-Lysine-N-Carboxyanhydride A. A mixture of N-ε-t-butyloxycarbonyl-L-lysine (1.23 g, 5.0 mmol) and chlorotrimethylsilane (1.08 g, 10.0 mmol) in tetrahydrofuran (50 mL) was cooled to 0° C. and a solution of triethylamine (1.01 g, 10.0 mmol) in 5 mL of tetrahydrofuran added dropwise. The mixture was stirred at 0° C. for 2.5 hours, filtered, and added to a solution of phosgene (10 mmol) in 15 mL of tetrahydrofuran. The temperature was raised to 60° C. and the solution was stirred for 2.0 hours, then overnight at ambient temperature. The volatiles were removed by rotary evaporation to give 0.79 g (58%) of N-ε-t-butyloxycarbonyl-L-lysine N-carboxyanhydride: IR($CH_2Cl_2$) 1860, 1795, 1710 cm$^{-1}$.

B. A mixture of N-ε-t-butyloxycarbonyl-L-lysine N-carboxyanhydride (0.79 g, 2.90 mmol) and 9-fluorenylmethyloxycarbonyl chloride (0.75 g, 2.90 mmol) in toluene (25 ml) was cooled to 0° C. and a solution of N-methylmorpholine (0.32 g, 3.2 mmol) in toluene (5 ml) added dropwise. The reaction was worked up as in Example IIIB to give 0.88 (66%) of N-α-(9-fluorenylmethyloxycarbonyl)-N-ε-t-butyloxycarbonyl-L-lysine-N-carboxyanhydride: mp 81°–85° C. (ethyl acetate/hexane); NMR ($CDCl_3$) δ 7.3–7.7 (m, 8H), 4.11–4.58 (m, 5H), 2.95–3.20 (m, 2H); 1.90–1.98 (m, 2H); 0.9–1.4 (m, 13H). Anal. Calcd for $C_{27}H_{30}N_2O_7$: C, 65.57; H, 6.11; N, 5.67. Found C, 66.33; H, 6.38; N, 5.67.

EXAMPLE V

N-Benzyloxycarbonyl-L-Alanine N-Carboxyanhydride

A solution of N-methylmorpholine (1.06 g, 10.5 mmol) in ethyl acetate (20 mL) was added dropwise to a mixture of L-alanine-N-carboxyanhydride (from IIA) (0.81 g, 7.0 mmol) and benzyloxycarbonyl chloride (1.89 g, 10.5 mmol) in ethyl acetate (80 mL) at 0° C. The reaction mixture was stirred for 1.5 h at 0° C., filtered, and the volume of the solution was reduced to 75 ml. Hexane (75 mL) was added with stirring, followed by cooling to −20° C., to give 1.20 g (71%) of N-benzyloxycarbonyl-L-alanine-N-carboxyanhydride: mp 101°–104° C.; NMR ($CDCl_3$) δ 7.33 (s, 5H), 5.27 (s, 2H), 4.60 (q, J=7 Hz, 1H), 1.61 (d, J=7 Hz, 3H). Anal. Calcd for $C_{12}H_{11}NO_5$: C, 57.83; H, 4.45; N, 5.62. Found: C, 57.60; H, 4.50; N, 5.53.

EXAMPLE VI

N-Benzyloxycarbonyl-L-Leucine-N-Carboxyanhydride

A solution of N-methylmorpholine (0.76 g, 7.50 mmol) in ethyl acetate (10 mL) was added dropwise to a solution of L-leucine N-carboxyanhydride (0.79 g, 5.0 mmol)(from IIIA) and benzyloxycarbonyl chloride (1.35 g, 7.50 mmol) in ethyl acetate (50 mL) at 0° C. The reaction mixture was stirred at 0° C. for 1.25 h, filtered and the volume of the solution was reduced to 5 mL. Hexane (50 mL) was added, followed by cooling to −20° C., to give 0.89 g (61%) of N-benzyloxycarbonyl-L-leucine-N-carboxyanhydride: mp 72°–73.5° C. (ether/hexane); NMR ($CDCl_3$) δ 7.40 (s, 5H), 5.33 (s, 2H), 4.71 (t, J=6 Hz, 1H), 1.80–2.04 (m, 3H), 0.91 (m, 6H). Anal. Calcd for $C_{15}H_{17}NO_5$: C, 61.84; H, 5.88; N, 4.81. Found: C, 61.64; H, 6.02; N, 4.90.

EXAMPLE VII

N-Phenyloxycarbonyl-L-Valine-N-Carboxyanhydride

A. L-Valine-N-carboxyanhydride was prepared from L-valine in 75% yield by the procedure described in Example IIA.

B. Example V was repeated substituting phenylchloroformate for benzylchloroformate and valine N-carboxyanhydride for leucine N-carboxyanhydride. The result was a 78% yield of N-phenyloxycarbonyl-L-valine-N-carboxyanhydride: mp 105°–106° C. (chloroform/hexane); NMR ($CDCl_3$) δ 7.30 (m, 5H), 4.70 (d, J=3.5 Hz, 1H), 2.60 (m, 1H), 1.22 (d, J=7 Hz, 3H), 1.07 (d, J=7 Hz, 3H), 1.07 (d, J=7 Hz, 3H). Anal. Calc for $C_{12}H_{13}NO_5$: C, 59.31 H, 4.98; N, 5.32. Found: C, 59.09; H, 4.91; N, 5.49.

EXAMPLE VIII

N-ethyloxycarbonyl-L-Alanine N-Carboxyanhydride

Example V was repeated substituting ethyl chloroformate for benzyl chloroformate. The result was a 62% yield of N-ethyloxycarbonyl-L-alanine N-carboxyanhydride: mp 72°–73.5° C. (ethyl acetate/hexane); NMR ($CDCl_3$) δ 4.73 (q, J=7 Hz, 2H), 4.33 (q, J=7 Hz, 1H), 1.70 (d, J=7 Hz, 3H), 1.33 (t, J=7 Hz, 3H). Anal. Calcd for $C_7H_9NO_5$: C, 44.92; H, 4.85; N, 7.49. Found: C, 45.08; H, 5.03; N, 7.33.

EXAMPLE IX

Benzyloxycarbonyl-L-Phenylalanine-N-Carboxyanhydride

A. L-Phenylalanine-N-carboxyanhydride was prepared from L-phenylalanine in 53% yield by the procedure of Example IIA.

B. To a solution of L-phenylalanine-N-carboxyanhydride (2.5 g, 13 mmol) and benzylchloroformate (3.4 g, 20 mmole) in ethyl acetate (130 mL) was added dropwise a solution of N-methylmorpholine (2.0 g, 20 mmol) in ethyl acetate (10 mL) at 0° C. The resulting mixture was stirred at 0° C. for 2.5 h and worked up as described in Example V to give 2.0 g (48%) of N-benzyloxycarbonyl-L-phenylalanine-N-carboxyanhydride: mp 108°–109° C.; NMR ($CDCl_3$) δ 7.35 (s, 5H), 7.00 (m, 5H), 5.31 (s, 2H), 4.83 (m, 1H), 3.28 (m, 2H), Anal. Calcd for $C_{18}H_{17}NO_5$: C, 68.13; H, 5.40; N, 4.42. Found: C, 68.11; H, 5.38; N, 4.20.

EXAMPLE X

Phenyloxycarbonyl-L-Alanine-N-Thiocarboxyanhydride

A. O-Ethyl-S-methylxanthate. To a solution of potassium ethylxanthate (16.0 g, 100 mmol) in water (50 mL) was added dropwise dimethyl sulfate (12.6 g, 100 mmol) at 4°±1° C. Upon completion of the addition, the reaction mixture was washed with dichloromethane (2×40 mL) and the combined organic fractions were dried ($MgSO_4$) and concentrated. The oily residue was dissolved in methanol and concentrated to give O-ethyl-S-methylxanthate of sufficient purity for use in the next step.

B. Ethoxythiocarbonyl-L-alanine. To the O-ethyl-S-methylxanthate prepared above was added a solution of L-alanine (8.9 g, 100 mmol) and NaOH (4.0 g, 100 mmol) in water (100 mL). The solution was heated to 45° C. for 2.3 h. While being purged with $N_2$, methanol (50 mL) was added and the mixture stirred at 45° C. an additional 0.7 h. The reaction mixture was allowed to cool to room temperature, washed with dichloromethane (3×25 mL), acidified to pH 2.5 with concentrated HCl, and extracted with ethyl acetate (2×50 mL). The combined organic solutions were dried ($MgSO_4$) and concentrated. Addition of hexane to the resulting oil gave 9.5 g (54%) of ethyloxythiocarbonyl-L-alanine as a colorless solid which melted at 74°–78° C. This material was further purified by recrystallization from ether/hexane: mp 77°–79° C.; IR ($CCl_4$) 3397, 1716 $cm^{-1}$.

C. L-Alanine-N-thiocarboxyanhydride. To a solution of ethyloxythiocarbonyl-L-alanine (3.0 g, 17 mmol) and imidazole (1.2 g, 17 mmol) in THF (20 mL) was added dropwise $PBr_3$ (5.4 g, 20 mmol) at 20° C. Stirring was continued until the solid mass had broken up into a fine suspension. The reaction mixture was poured into a mixture of saturated $NaHCO_3$ (200 mL) and ethyl acetate (150 mL). The organic layer was separated, washed with 1M HCl(2×100 mL), saturated $NaHCO_3$ (100 mL), and brine (100 mL), dried ($MgSO_4$), and concentrated. The resulting oil solidified on standing. Recrystallization of the solid gave 0.75 g (34%) of L-alanine-N-thiocarboxyanhydride: mp 91°–92° C.; IR ($CCl_4$) 1750, 1695 $cm^{-1}$.

D. Phenyloxycarbonyl-L-alanine-N-thiocarboxyanhydride. To a solution of L-alanine-N-thiocarboxyanhydride (0.49 g, 3.8 mol) in 50 mL of ethyl acetate was added phenyl chloroformate (0.95 g, 6.1 mmol) at 0° C., followed by dropwise addition of a solution of N-methylmorpholine (0.57 g, 5.6 mmol) in ethyl acetate (10 mL) at 0° C. The resulting mixture was stirred for 3 h at 0° C., filtered and concentrated to a white semi-solid. The semi-solid material was dissolved in 20 mL of ethyl acetate, hexane (150 mL) was added, and the mixture cooled to −20° C. to give 0.55 g (62%) of phenyloxycarbonyl-L-alanine-N-thiocarboxyanhydride: mp 110°–111° C.; NMR (CDCl$_3$) δ 7.18 (m, 5H), 4.83 (q, 1H, J=7 Hz), 1.71 (d, 3H, J=7 Hz); IR (CH$_2$Cl$_2$) 1810, 1740 (doublet), 1715 (Shoulder). Anal. Calcd for C$_{11}$H$_9$NO$_4$S: C, 52.58; H, 3.61; N, 5.58; S, 12.76. Found: C, 52.75; H, 3.72; N, 5.36; S, 12.98.

EXAMPLE XI

N-(9-Fluorenylmethyloxycarbonyl)-O-t-Butyl-L-Threonine-N-Carboxyanhydride

A. O-t-Butyl-L-threonine N-carboxyanhydride was prepared from O-t-butyl-L-threonine in 57% yield using the trimethylsilyl procedure described in Example IVA.

B. To a solution of O-t-butyl-L-threonine-N-carboxyanhydride (0.80 g, 4.0 mmol) and 9-fluorenylmethyloxycarbonyl chloride (1.0 g, 4.0 mmol) in toluene (50 mL) was added dropwise a solution of N-methylmorpholine (0.49 g, 4.8 mmol) in 8 mL of toluene at 0° C. The reaction was stirred for 3 h at 0° C., filtered, and the volatiles removed under reduced pressure. The residue was crystallized from ether/hexane to give 1.0 g (60%) of N-(9-fluorenylmethyloxycarbonyl)-O-t-butyl-L-threonine: mp 124°–127° C.; NMR (CDCl$_3$) δ 7.08–7.78 (m, 8H), 4.05–4.61 (m, 4H), 1.18 (s, 9H), 1.16 (d, 3H, J=7 Hz). Anal. Calcd for C$_{24}$H$_{25}$NO$_6$: C, 68.07; H, 5.95; N, 3.31. Found: C, 67.89; H, 5.96; N, 3.28.

EXAMPLE XII

Ethyloxycarbonyl-α-Aminoisobutyric Acid-N-Carboxyanhydride

A. α-Aminoisobutyric acid N-carboxyanhydride was prepared in 67% by the procedure described in Example IIA.

B. Example VIIIB was repeated substituting α-aminoisobutyric acid N-carboxyanhydride for L-alanine-N-carboxyanhydride to give a 16% yield of ethyloxycarbonyl-α-aminoisobutyric acid N-carboxyanhydride: mp 68°–70° C. (chloroform/hexane); NMR (CCl$_4$) δ 4.59 (q, 2H, J=7 Hz), 2.00 (s, 6H), 1.65 (t, 3H, J=7 Hz). Anal Calcd for C$_8$H$_{11}$NO$_5$: C, 47.76; H, 5.51; N, 6.96. Found: C, 47.67; H, 5.51; N, 7.14.

EXAMPLE XIII

N-t-Butyloxycarbonyl-L-Alanine N-Carboxyanhydride

To a solution of t-butyl alcohol (1.25 g, 16.9 mmol) and phosgene (3.4 mL of a 5M solution in dioxane, 17 mmol) in 80 mL of ethyl acetate was added dropwise N-methylmorpholine (3.4 g, 34 mmol) at −50° C. The reaction mixture was stirred for 0.5 h. L-alanine-N-carboxyanhydride (0.23 g, 2.0 mmol) in ethyl acetate (10 mL) was added and the mixture stirred at −50° C. for an additional 0.75 h. N-Methylmorpholine (1.0 g, 10 mmol) was added, and stirring was continued for another 0.75 h at −50° C. The solids were removed by filtration, the solution was concentrated, and the product was obtained after trituration with hexane. Recrystallization from toluene gave 0.28 g (65%) of N-t-butyloxycarbonyl-L-alanine-N-carboxyanhydride. mp 103°–104.5° C.; NMR (CDCl$_3$) δ 4.71 (q, 1H, J=7 Hz), 1.80 (d, 3H, J=7 Hz), 1.70 (s, 9H). Anal. Calcd for C$_8$H$_{13}$NO$_5$: C, 50.23; H, 6.09; N, 6.51. Found: C, 50.66; H, 6.36; N, 6.38.

EXAMPLE XIV

N-(t-Butyloxycarbonyl)-O-Benzyl-L-Serine-N-Carboxyanhydride

A. O-Benzyl-L-serine-N-carboxyanhydride was prepared in 68% yielded by the procedure of Example IIA.

B. Example XIII was repeated substituting O-Benzyl-L-serine-N-carboxyanhydride for L-alanine-N-carboxyanhydride to give N-(t-butyloxycarbonyl)-O-benzyl-L-serine-N-carboxyanhydride in 52% yield: mp 98°–99.5° C.; NMR (CCl$_4$) δ 7.30 (m, 5H), 4.64 (m, 3H, benzyl CH$_2$ and NCA ring proton), 4.09 (dd, 1H, J=15, 5 Hz), 3.88 (dd, 1H, J=15, 5 Hz), 1.65 (s, 9H); Anal. Calcd for C$_{15}$H$_{19}$NO$_6$: C, 59.80; H, 5.96; N, 4.36. Found: C, 59.71; H, 6.25; N, 4.05.

EXAMPLE XV

Phenyloxycarboxyl Derivation of 1-Amino-1-Cyclohexanecarboxylic Acid N-Carboxyanhydride A. 1-Amino-1-cyclohexanecarboxylic acid-N-carboxyanhydride was prepared from 1-amino-1-cyclohexanecarboxylic acid in 50% yield by the procedure described in Example IIA.

B. To a solution of the N-carboxyanhydride prepared in A (0.85 g, 5.0 mmol) and phenyl chloroformate (1.2 g, 7.5 mmol) in ethyl acetate (30 mL) at 0° C. was added a solution of N-methylmorpholine (0.76 g, 7.5 mmol) in 8 mL of ethylacetate. The reaction mixture was stirred for 2 h at 0° C., filtered, and concentrated. The white, semi-solid residue was recrystallized from ethyl ether/methylene chloride/hexane to give 0.92 g (66%) of the N-carboxyanhydride: mp 156.5°–158° C.; NMR (CDCl$_3$) δ 7.28 (m, 5H), 1.20–3.10 (m, 10H). Anal. Calcd for C$_{15}$H$_{15}$NO$_5$: C, 62.27; H, 5.23; N, 4.84. Found: C, 62.03; H, 5.22; N, 4.77.

EXAMPLE XVI

L-Leucyl-L-Valine

9-Fluorenylmethyloxycarbonyl-L-valine esterified to p-alkoxybenzyl alcohol derivitized 2% crosslinked polystyrene (0.25 gm, 0.13 mmol valine) was placed in a solid phase peptide synthesis vessel. Dimethylformamide (5 mL) was added and the slurry was shaken for 30 min. The dimethylformamide was removed and the swollen resin treated twice with 10% piperidine in dimethylformamide (5 mL for 5 min followed by 5 mL for 15 min) to remove the 9-fluorenylmethyloxycarbonyl protecting group. The resin was washed with dimethylformamide (4×5 mL) and reacted with 9-fluorenylmethyloxycarbonyl-L-leucine-N-carboxyanhydride (145 mg, 0.38 mmol) in dimethylformamide (6 mL) for 45 min. The fluorenylmethyloxycarbonyl protecting group was removed as above and the resin washed with dimethylformamide (3×5 mL) and methylene chloride (3×5 mL). The resulting dipeptide was cleaved from the resin by treatment with methylene chloride/trifluoroacetic acid (6 mL, 1/1) for 45 min. The solution was removed and the resin washed with methylene chloride (3×5 mL) and methanol (2×5 mL). The combined solution and washes were evaporated in vacuo to a semi-solid, which was taken up in distilled water and filtered. The aqueous solution was freeze-dried, the resulting solid triturated with ether(3×) to remove resin related contaminants, and dried under reduced pressure to give L-leucyl-L-valine in >90% yield. The identity of the dipeptide was confirmed by HPLC analysis (flow rate=1.5 mL/min, detection at 215 nm, 30% methanol in 0.5M perchloric acid) by co-elution with a known standard (Retn. time 8.49 minutes). The purity was determined to be >97%, with all contaminants being traceable to the resin. No D-leucyl-L-valine (Retn. time 32 minutes) could be detected (detection limits <0.1%).

EXAMPLE XVII

L-Leucyl-L-Valine

Example XVI was repeated except that 9-fluorenylmethyloxycarbonyl-L-leucine-N-carboxyanhydride was reacted with the free amine of L-valine on the resin using methylene chloride (5 mL) instead of dimethylformamide as the solvent. The results were comparable to Example XVI.

EXAMPLE XVIII

L-Leucyl-L-Alanyl-L-Valine (FMOC Procedure)

The procedure of Example XVI was used to prepare L-leucyl-L-alanyl-L-valine. After cleavage from the resin and ether washes the tripeptide was obtained in >88% yield as a white solid. HPLC analysis, using conditions described in Example XVI confirmed the identity of the product which co-eluded with a known standard. (Rtn. time 16.28 min.) Deletion sequences such as L-leucyl-L-valine and L-alanyl-L-valine were not detected (detection limits <0.1%).

EXAMPLE XIX

L-Leucyl-L-Alanyl-L-Valine (Boc Procedure)

t-Butyloxycarbony-L-valine esterified to methylated 2% crosslinked polystyrene (i.e. Merryfield resin) (0.50 gm, 0.23 mmol valine) was placed in a solid phase peptide synthesis vessel. Methylene chloride (5 mL) was added and the slurry shaken for 30 minutes. The solvent was removed and the resin treated with methylene chloride/trifluoroacetic acid (6 mL of 1/1) for 30 min to remove the t-butyloxycarbonyl protecting group. The resin was washed with methylene chloride (3×5 mL) neutralized with 10% triethylamine in methylene chloride (5 mL), washed with methylene chloride (3×5 mL) and then reacted with a solution of t-butyloxycarbonyl-L-alanine-N-carboxyanhydride (200 mg, 1.0 mmol) in methylene chloride (5 mL) for 45 min. The resulting protected dipeptide resin was washed with methylenechloride (3×5 mL). The resin was again deblocked, washed, neutralized and washed as described above. t-Butyloxycarbonyl-L-leucine-N-carboxyanhydride (240 mg, 1.0 mmol) in methylene chloride (6 mL) was added to the resin and the mixture shaken for 45 min. The solution was removed and the resin washed with methylene chloride (3×5 mL), methanol (3×5 mL) and methylene chloride (3×5 mL) and dried under high vacuum. The t-butyloxycarbonyl protected tripeptide resin was reacted with liquid hydrogen fluoride at 0° C. for 30 minutes. The hydrogen fluoride was removed and the residue dried under high vacuum. The peptide was taken up in water and the resin removed by filtration. The solution was freeze-dried to give a nearly quantitative yield of L-leucyl-L-alanyl-L-valine. HPLC analysis results were comparable to Example XVIII.

EXAMPLE XX

L-Alanyl-L-Phenylalanine (Via Full Protection Procedure)

A. To L-phenylalanine benzyl ester p-toluenesulfonate (1.07 g, 2.5 mmol) in tetrahydrofuran (20 mL) at 0° C. was added N-methylmorpholine (0.25 g, 2.5 mmol). The mixture was stirred 0.5 h at 0° C. and N-benzyloxycarbonyl-L-alanine-N-carboxyanhydride (0.50 g 2.0 mmol) was added. The reaction mixture was stirred 2 h at 0° C. and water (20 mL) and dichloromethane (50 mL) were added. The layers were separated and the aqueous layer washed with dichloromethane (25 mL). The combined organic fractions were washed with 0.5M HCl (2×50 mL), 10% sodium bicarbonate (50 mL), and water (2×50 mL), dried (MgSO$_4$), and concentrated. Crystallization occurred upon addition of hexane to give 0.66 g (72%) of N-benzyloxycarbonyl-L-alanyl-L-phenylalanine benzyl ester: mp 118.5°–119° C.; NMR (CDCl$_3$) δ 7.64 (s, 1H), 6.82–7.39 (m, 6H), 5.04 (s, 2H), 5.00 (s, 2H), 4.58–4.92 (m, 2H), 3.07 (d, J=6 Hz, 2H) 1.29 (d, J=7 Hz, 3H).

B. A mixture of N-benzyloxycarbonyl-L-alanyl-L-phenylalanine benzyl ester (0.50 g, 1.1 mmol) and 10% Pd palladium on carbon (0.1 g) in ethyl alcohol (150 mL) was shaken on a Parr hydrogenation apparatus for 6.5 h at 20° C. The reaction mixture was filtered and the filtrate rinsed with water (100 mL). The solution was concentrated to give 0.26 g (100%) of L-alanyl-L-phenylalanine. HPLC analysis showed >99% purity and no evidence of racemization.

EXAMPLE XXI

L-Alanyl-L-Phenylalanine (Via Partial Protection Procedure)

A. To a solution of L-phenylalanine (0.33 g, 2.0 mmol) in 0.20M potassium carbonate (20 mL) and acetonitrile (30 mL) was added dropwise a solution of N-benzyloxycarbonyl-L-alanine N-carboxyanhydride (0.45 g, 1.8 mmol) in acetonitrile (5 mL) at 0° C. The mixture was stirred 40 min at 0° C. and diluted with ethyl acetate (50 mL) and 1M hydrochloric acid (10 mL). The layers were separated and the aqueous layer extracted with ethyl acetate (2×35 mL). The combined organic fractions were washed with brine (30 mL), 0.5M hydrochloric acid (2×50 mL) and water (2×50 mL), dried (MgSO$_4$) and concentrated. The residue was recrystallized from chloroform/hexane to give 0.26 g (39%) of N-benzyloxycarbonyl-L-alanyl-L-phenylalanine: mp 121°–122° C.; NMR (DMSO-d$_6$) δ 12.71 (s, 1H), 8.06 (m, 1H), 7.30 (m, 5H), 5.01 (s, 2H), 4.43 (m, 1H), 4.06 (m, 1H), 2.99 (m, 2H), 11.19 (d, 2H, J=7 Hz).

B. A mixture of N-benzyloxycarbonyl-L-alanyl-L-phenylalanine (0.208 g, 0.562 mmol) and 10% Pd on carbon (0.1 g) in 95% ethyl alcohol (50 mL) was shaken on a Parr hydrogenation apparatus for 16 h at 20° C. The reaction mixture was filtered and the filtrate rinsed with water (100 mL). The combined solutions were concentrated to give 0.122 g (92%) of L-alanyl-L-phenylalanine as a white solid. HPLC analysis showed >99.5% purity and no evidence of racemization.

It is claimed:

1. A urethane-protected amino acid-N-carboxyanhydride or N-thiocarboxyanhydride having the structure:

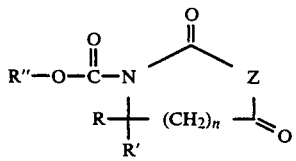

wherein
R and R' are hydrogen, alkyl, cycloalkyl, substituted alkyl, substituted cycloalkyl, aryl, or substituted aryl and at least one of R and R' is other than hydrogen; R" is alkyl, aryl, substituted alkyl or substituted aryl; Z is oxygen or sulfur; and n is 0, 1 or 2.

2. A urethane-protected amino acid-N-carboxyanhydride or N-thiocarboxyanhydride according to claim 1 wherein R" is an alkyl of 1 to 20 carbon atoms.

3. A urethane-protected amino acid-N-carboxyanhydride or N-thiocarboxyanhydride according to claim 2 wherein R" is lower alkyl or substituted lower alkyl.

4. A urethane-protected amino acid-N-carboxyanhydride or N-thiocarboxyanhydride according to claim 3 wherein R" is t-butyl.

5. A urethane-protected amino acid-N-carboxyanhydride or N-thiocarboxyanhydride according to claim 1 wherein R" is aryl or substituted aryl.

6. A urethane-protected amino acid-N-carboxyanhydride or N-thiocarboxyanhydride according to claim 5 wherein R" is phenyl or substituted phenyl.

7. A urethane-protected amino acid-N-carboxyanhydride or N-thiocarboxyanhydride according to claim 1 wherein R" is aralkyl or substituted aralkyl.

8. A urethane-protected amino acid-N-carboxyanhydride or N-thiocarboxyanhydride according to claim 7 wherein R" is benzyl or substituted benzyl.

9. A urethane-protected amino acid-N-carboxyanhydride or N-thiocarboxyanhydride according to claim 8 wherein R" is p-methoxybenzyl.

10. A urethane-protected amino acid-N-carboxyanhydride or N-thiocarboxyanhydride according to claim 7 wherein R" is 9-fluorenylmethyl or substituted 9-fluorenylmethyl.

11. A urethane-protected amino acid N-carboxyanhydride or N-thiocarboxyanhydride according to claim 1 wherein at least one of R or R' is the side chain of a protected or unprotected amino acid.

12. A urethane-protected amino acid N-carboxyanhydride or N-thiocarboxyanhydride according to claim 11 wherein R or R' is the side chain of alanine.

13. A urethane-protected amino acid N-carboxyanhydride or N-thiocarboxyanhydride according to claim 11 wherein R or R' is the side chain of arginine or suitably protected arginine.

14. A urethane-protected amino acid N-carboxyanhydride or N-thiocarboxyanhydride according to claim 11 wherein R or R' is the side chain of aspartic acid or suitably protected aspartic acid.

15. A urethane-protected amino acid N-carboxyanhydride or N-thiocarboxyanhydride according to claim 11 wherein R or R' is the side chain of asparagine or suitably protected asparagine.

16. A urethane-protected amino acid N-carboxyanhydride or N-thiocarboxyanhydride according to claim 11 wherein R or R' is the side chain of cysteine or suitably protected cysteine.

17. A urethane-protected amino acid N-carboxyanhydride or N-thiocarboxyanhydride according to claim 11 wherein R or R' is the side chain of cystine.

18. A urethane-protected amino acid N-carboxyanhydride or N-thiocarboxyanhydride according to claim 11 wherein R or R' is the side chain of glutamic acid or suitably protected glutamic acid.

19. A urethane-protected amino acid N-carboxyanhydride or N-thiocarboxyanhydride according to claim 11 wherein R or R' is the side chain of glutamine or suitably protected glutamine.

20. A urethane-protected amino acid N-carboxyanhydride or N-thiocarboxyanhydride according to claim 11 wherein R or R' is the side chain of histidine or suitably protected histidine.

21. A urethane-protected amino acid N-carboxyanhydride or N-thiocarboxyanhydride according to claim 11 wherein R or R' is the side chain of isoleucine.

22. A urethane-protected amino acid N-carboxyanhydride or N-thiocarboxyanhydride according to claim 11 wherein R or R' is the side chain of a suitably protected lysine.

23. A urethane-protected amino acid N-carboxyanhydride or N-thiocarboxyanhydride according to claim 11 wherein R or R' is the side chain of leucine.

24. A urethane-protected amino acid N-carboxyanhydride or N-thiocarboxyanhydride according to claim 11 wherein R or R' is the side chain of methionine.

25. A urethane-protected amino acid N-carboxyanhydride or N-thiocarboxyanhydride according to claim 11 wherein R or R' is the side chain of norleucine.

26. A urethane-protected amino acid N-carboxyanhydride or N-thiocarboxyanhydride according to claim 11 wherein R or R' is the side chain of a suitably protected ornithine.

27. A urethane-protected amino acid N-carboxyanhydride or N-thiocarboxyanhydride according to claim 11 wherein R or R' is the side chain of phenylalanine.

28. A urethane-protected amino acid N-carboxyanhydride or N-thiocarboxyanhydride according to claim 11 wherein R or R' is the side chain of serine or suitably protected serine.

29. A urethane-protected amino acid N-carboxyanhydride or N-thiocarboxyanhydride according to claim 11 wherein R or R' is the side chain of threonine or suitably protected threonine.

30. A urethane-protected amino acid N-carboxyanhydride or N-thiocarboxyanhydride according to claim 11 wherein R or R' is the side chain of tryptophan or suitably protected tryptophan.

31. A urethane-protected amino acid N-carboxyanhydride or N-thiocarboxyanhydride according to claim 11 wherein R or R' is the side chain of tyrosine or suitably protected tyrosine.

32. A urethane-protected amino acid N-carboxyanhydride or N-thiocarboxyanhydride according to claim 11 wherein R or R' is the side chain of valine.

33. A urethane-protected amino acid N-carboxyanhydride or N-thiocarboxyanhydride according to claim 11 wherein R or R' is the side chain of homoserine or suitably protected homoserine.

34. N-9-fluorenylmethyloxycarbonyl-L-leucine-N-carboxyanhydride.

35. N-9-fluorenylmethyloxycarbonyl-L-alanine-N-carboxyanhydride.

36. N-α-(9-fluorenylmethyloxycarbonyl)-N-ε-t-butyloxycarbonyl-L-lysine-N-carboxyanhydride.

21

37. N-benzyloxycarbonyl-L-alanine-N-carboxyanhydride.
38. N-benzyloxycarbonyl-L-leucine-N-carboxyanhydride.
39. N-phenyloxycarbonyl-L-valine-N-carboxyanhydride.
40. N-ethyloxycarbonyl-L-alanine-N-carboxyanhydride.
41. N-benzyloxycarbonyl-L-phenylalanine-N-carboxyanhydride.
42. N-phenyloxycarbonyl-L-alanine-N-thiocarboxyanhydride.
43. N-(9-fluorenylmethyloxycarbonyl)-O-t-butyl-L-threonine-N-carboxyanhydride.
44. N-9-fluorenylmethyloxycarbonyl-β-alanine-N-carboxyanhydride.
45. N-t-butyloxycarbonyl-L-alanine-N-carboxyanhydride.
46. N-(t-butyloxycarbonyl)-O-benzyl-L-serine-N-carboxyanhydride.
47. N-phenyloxycarbonyl-1-amino-1-carboxy cyclohexane-N-carboxyanhydride.
48. N-ethyloxylcarbonyl-α-aminoisobutyric acid-N-carboxyanhydride.
49. A method for the synthesis of a polypeptide chain wherein an amino acid component is allowed to react with a second similar or dissimilar amino acid component and the process repeated until the desired polypeptide is obtained, the improvement comprising using as the protected amino acid component in at least one of said reactions a compound having the structure:

$$R''-O-\underset{\underset{O}{\|}}{C}-N\underset{R-\underset{R'}{\overset{|}{\longmapsto}}(CH_2)_n}{\overset{\overset{O}{\|}}{\diagdown}}\underset{O}{\overset{Z}{\diagup}}$$

wherein
R and R' are hydrogen, alkyl, aryl, substituted alkyl, or substituted aryl and at least one of R and R' is other than hydrogen; R" is alkyl, aryl, substituted alkyl or substituted aryl; Z is oxygen or sulfur; and n is 0, 1 or 2.
50. A method according to claim 49 wherein R" is an alkyl, or substituted alkyl of 1 to 20 carbon atoms.
51. A method according to claim 50 wherein R" is lower alkyl or substituted lower alkyl.
52. A method according to claim 50 wherein R" is t-butyl.
53. A method according to claim 49 wherein R" is aryl or substituted aryl.
54. A method according to claim 53 wherein R" is phenyl or substituted phenyl.
55. A method according to claim 49 wherein R" is aralkyl or substituted aralkyl.
56. A method according to claim 55 wherein R" is benzyl or substituted benzyl.
57. A method according to claim 55 wherein R" is p-methoxybenzyl.
58. A method according to claim 55 wherein R" is 9-fluorenylmethyl or substituted 9-fluorenylmethyl.
59. A method according to claim 49 wherein at least one of R or R' is the side chain of a protected or unprotected amino acid.
60. A method for the solid phase synthesis of a polypeptide chain on a soluble or insoluble support wherein a protected amino acid component is coupled by condensation reaction to the support containing substituent groups reactive with the carboxyl terminus end of said amino acid component. The coupled protected amino acid component is deprotected, neutralized if necessary, and a second similar or dissimilar protected amino acid component coupled to said deprotected amino acid compound, and the process repeated until the desired polypeptide is obtained, the improvement comprising using as the protected amino acid component in at least one of said reactions a compound having the structure:

$$R''-O-\underset{\underset{O}{\|}}{C}-N\underset{R-\underset{R'}{\overset{|}{\longmapsto}}(CH_2)_n}{\overset{\overset{O}{\|}}{\diagdown}}\underset{O}{\overset{Z}{\diagup}}$$

wherein
R and R' are hydrogen, alkyl, cycloakyl, substituted alkyl, substituted cycloalkyl, aryl, or substituted aryl; R" is alkyl, aryl, substituted alkyl or substituted aryl; Z is oxygen or sulfur; and n is 0, 1 or 2.
61. A method according to claim 60 wherein R" is an alkyl or substituted alkyl of 1 to 20 carbon atoms.
62. A method according to claim 61 wherein R" is lower alkyl or substituted lower alkyl.
63. A method according to claim 62 wherein R" is t-butyl.
64. A method according to claim 60 wherein R" is aryl or substituted aryl.
65. A method according to claim 64 wherein R" is phenyl or substituted phenyl.
66. A method according to claim 60 wherein R" is aralkyl or substituted aralkyl.
67. A method according to claim 66 wherein R" is benzyl or substituted benzyl.
68. A method according to claim 66 wherein R" is p-methoxybenzyl.
69. A method according to claim 66 wherein R" is 9-fluorenylmethyl or substituted 9-fluorenylmethyl.
70. A method according to claim 60 wherein at least one of R or R' is the side chain of a protected or unprotected amino acid.
71. A method of preparing urethane-protected amino acid N-carboxyanhydrides or N-thiocarboxyanhydrides having the structure:

$$R''-O-\underset{\underset{O}{\|}}{C}-N\underset{R-\underset{R'}{\overset{|}{\longmapsto}}(CH_2)_n}{\overset{\overset{O}{\|}}{\diagdown}}\underset{O}{\overset{Z}{\diagup}}$$

wherein
R and R' are hydrogen, alkyl, cycloalkyl, substituted alkyl, substituted cycloalkyl, aryl, or substituted aryl; R" is alkyl, aryl, substituted alkyl or substituted aryl; Z is oxygen or sulfur; and n is 0, 1 or 2, comprising reacting an amino acid N-carboxyanhydride or N-thiocarboxyanhydride having the structure:

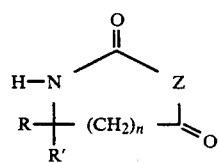

wherein R, R', Z and n are as designated above, with a haloformate having the structure:

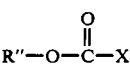

wherein X is halogen and R'' is as designated above, in an inert diluent, under anhydrous conditions and in the presence of N-methylmorpholine.

72. A method according to claim 71 wherein the urethane-protected amino acid N-carboxyanhydride reaction product is recovered by crystallization.

* * * * *